(12) United States Patent
Sweitzer et al.

(10) Patent No.: US 12,109,130 B2
(45) Date of Patent: Oct. 8, 2024

(54) SURGICAL EXTRACTOR

(71) Applicant: Shukla Medical, St. Petersburg, FL (US)

(72) Inventors: Zachary Robert Sweitzer, Keyport, NJ (US); Adam Gosik-Wolfe, Tampa, FL (US)

(73) Assignee: Shukla Medical, St. Petersburg, FL (US)

( * ) Notice: Subject to any disclaimer, the term of this patent is extended or adjusted under 35 U.S.C. 154(b) by 18 days.

(21) Appl. No.: 17/149,342

(22) Filed: Jan. 14, 2021

(65) Prior Publication Data

US 2021/0212841 A1     Jul. 15, 2021

Related U.S. Application Data

(60) Provisional application No. 63/043,229, filed on Jun. 24, 2020, provisional application No. 62/960,979, filed on Jan. 14, 2020.

(51) Int. Cl.
*A61F 2/46*     (2006.01)
*A61B 17/92*    (2006.01)

(52) U.S. Cl.
CPC ............ *A61F 2/4612* (2013.01); *A61B 17/92* (2013.01); *A61F 2002/4619* (2013.01); *A61F 2002/4625* (2013.01); *A61F 2002/4627* (2013.01); *A61F 2002/4628* (2013.01)

(58) Field of Classification Search
CPC ........ A61F 2002/4619; A61F 2002/462; A61F 2002/4622; A61F 2002/4625; A61F 2002/4627; A61F 2002/4628; A61F 2/4607; A61F 2/4612; A61F 2/4603; A61B 17/92

See application file for complete search history.

(56) References Cited

U.S. PATENT DOCUMENTS

| | | | |
|---|---|---|---|
| 1,534,992 A | 4/1925 | Reeves | |
| 5,282,805 A | 2/1994 | Richelsoph | |
| 5,849,015 A * | 12/1998 | Haywood | A61F 2/4607 606/99 |
| 6,017,342 A | 1/2000 | Rinner | |
| 2004/0059271 A1 | 3/2004 | Berry | |
| 2005/0033290 A1 | 2/2005 | Nevelos | |
| 2005/0209597 A1* | 9/2005 | Long | A61F 2/4609 606/86 R |
| 2006/0074432 A1* | 4/2006 | Stad | A61F 2/4611 606/90 |
| 2007/0163084 A1 | 7/2007 | Liou | |

(Continued)

OTHER PUBLICATIONS

United States Patent and Trademark Office, Office Action in U.S. Appl. No. 17/148,933, dated Mar. 11, 2024.

(Continued)

*Primary Examiner* — Amy R Sipp
(74) *Attorney, Agent, or Firm* — Kim IP Law Group LLC

(57) ABSTRACT

A surgical extractor that includes a first arm and a second arm, a linkage assembly connected to the first and second arms, and a driven shaft operatively engaged with the linkage assembly for moving the linkage assembly between first and second positions. The surgical extractor further includes a tensioning shaft engageable with the driven shaft for moving the driven shaft relative to the linkage assembly.

21 Claims, 19 Drawing Sheets

(56) References Cited

U.S. PATENT DOCUMENTS

| | | | |
|---|---|---|---|
| 2011/0301613 A1* | 12/2011 | Green, II | A61B 17/921 606/99 |
| 2012/0253469 A1* | 10/2012 | Collins | A61F 2/4603 623/23.15 |
| 2016/0228262 A1 | 8/2016 | Bailey | |
| 2017/0156751 A1* | 6/2017 | Csernatoni | A61B 17/8802 |
| 2018/0125674 A1 | 5/2018 | Liu | |
| 2018/0125677 A1 | 5/2018 | Burrows-Ownbey | |

OTHER PUBLICATIONS

United States Patent and Trademark Office, Office Action in U.S. Appl. No. 17/148,933, dated Nov. 23, 2023.

* cited by examiner

SURGICAL EXTRACTOR

CROSS-REFERENCE TO RELATED APPLICATIONS

This application claims the benefit under 35 U.S.C. § 119(e) to U.S. Provisional Application No. 62/960,979, filed Jan. 14, 2020, and entitled "Medical Device Instrument," and U.S. Provisional Application No. 63/043,229, filed Jun. 24, 2020, and entitled "Medical Implant Extractor," the entire disclosures of each of which are hereby incorporated by reference for all purposes.

BACKGROUND OF THE DISCLOSURE

The exemplary embodiments of present invention relate generally to a surgical extractor and, more specifically, to an instrument for extracting an implant including, without limitation, a glenosphere implant, from bone.

SUMMARY OF THE DISCLOSURE

In accordance with an exemplary embodiment of the subject disclosure, there is provided a surgical extractor comprising: a first arm and a second arm; a linkage assembly connected to the first and second arms; a driven shaft operatively engaged with the linkage assembly for moving the linkage assembly between first and second positions; and a tensioning shaft engageable with the driven shaft for moving the driven shaft relative to the linkage assembly. The tensioning shaft is axially movable relative to the linkage assembly.

The surgical extractor further comprises a housing containing the tensioning shaft and the driven shaft. The tensioning shaft is movable within the housing between first and second positions. The tensioning shaft extends through a proximal end of the housing and the driven shaft extends through a distal end of the housing. The housing further comprises a locking mechanism for releasably securing the tensioning shaft within the housing. The tensioning shaft includes an annular groove that engages the locking mechanism for locking the position of the tensioning shaft within the housing. The linkage assembly comprises a central link housing the driven shaft. The central link is threadedly engaged with the driven shaft. The linkage assembly comprises a plurality of links including: a central link; a first triangular link having a first corner pivotably connected to a first side of the central link, and a second corner pivotably connected to the first arm; a second triangular link having a first corner pivotably connected to a second side of the central link, and a second corner pivotably connected to the second arm; a first drive link having a distal end pivotably connected to a third corner of the first triangular link and a proximal end; and a second drive link having a distal end pivotably connected to a third corner of the second triangular link and a proximal end. The surgical extractor further comprises: a first strut link having a proximal end pivotably connected to the first side of the central link and a distal end pivotably connected to the first arm; and a second strut link having a proximal end pivotably connected to the second side of the central link and a distal end pivotably connected to the second arm. A proximal end of the driven shaft includes a socket. A distal end of the tensioning shaft includes a driver head for operatively engaging the driven shaft. The surgical extractor further comprises: a first jaw attachable to a distal end of the first arm; and a second jaw attachable to a distal end of the second arm. The surgical extractor further comprises a push-to-connect assembly for releasably connecting the first jaw to the first arm. The surgical extractor further comprises a handle assembly attachable to the tensioning shaft. The handle assembly includes a T-handle having a handle and a through hole about a lateral end thereof. The surgical extractor further comprises a strike plate extending from a proximal end of the tensioning shaft.

In accordance with another exemplary embodiment of the subject disclosure, there is provided a surgical extractor for extracting orthopedic implants comprising: a housing; a first arm and a second arm; a linkage assembly connected to the first and second arms; a driven shaft housed within the housing and operatively engaged with the linkage assembly for moving the linkage assembly; and a tensioning shaft housed within the housing and engageable with the driven shaft for moving the driven shaft relative to the linkage assembly, wherein the linkage assembly includes: a central link, a first triangular link having a first corner pivotably connected to a first side of the central link, and a second corner pivotably connected to the first arm, a second triangular link having a first corner pivotably connected to a second side of the central link, and a second corner pivotably connected to the second arm, a first drive link having a distal end pivotably connected to a third corner of the first triangular link and a proximal end pivotably connected to the housing, and a second drive link having a distal end pivotably connected to a third corner of the second triangular link and a proximal end pivotably connected to the housing.

The driven shaft threadedly engages the central link to move between first and second positions, wherein in the first position the first and second arms are spaced apart a first distance and in the second position, the first and second arms are spaced apart a second distance less than the first distance.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, +10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1:
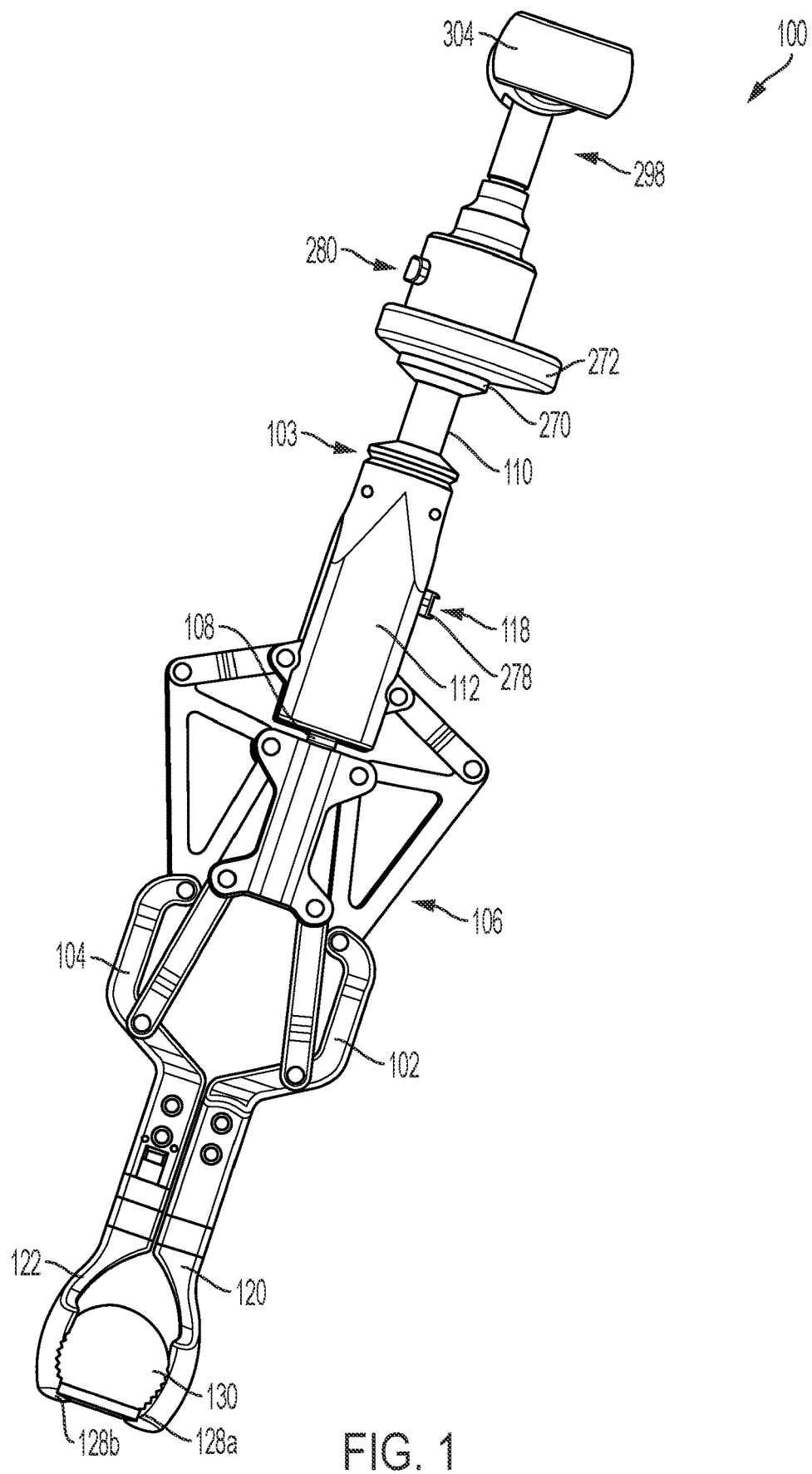
FIG. 1 is a perspective view of a surgical extractor in accordance with an exemplary embodiment of the subject disclosure.
Figure 2:
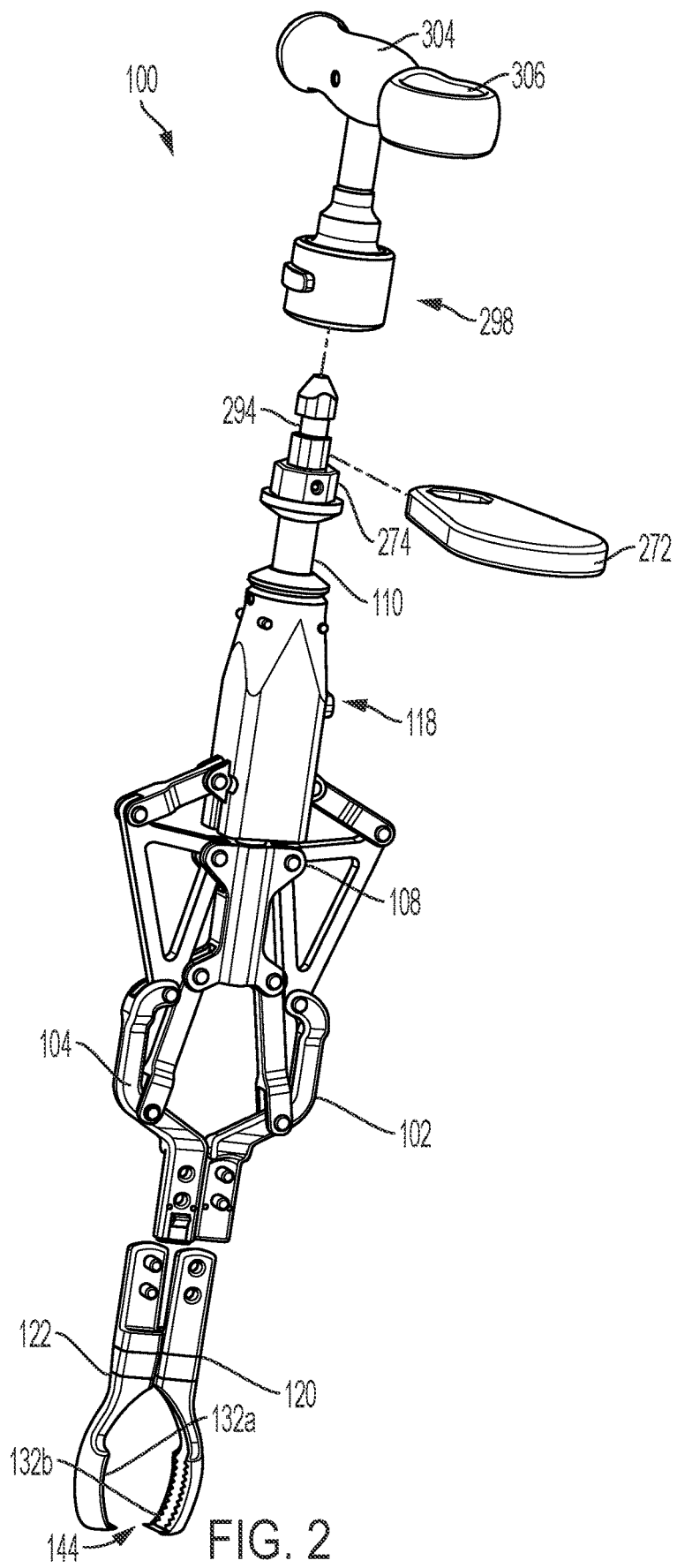
FIG. 2 is a partially exploded perspective view of the surgical extractor of FIG. 1.

Referring now to the drawings, FIGS. 1 and 2 disclose a surgical extractor 100 according to an exemplary embodiment of the subject disclosure. The surgical extractor 100 includes a first arm 102, a second arm 104, and a linkage assembly 106 connected to the first and second arms. The surgical extractor 100 further includes a driven shaft 108 operatively engaged with the linkage assembly 104 and a tensioning shaft 110 engageable with the driven shaft 108 for moving the driven shaft relative to the linkage assembly.

Figure 3:
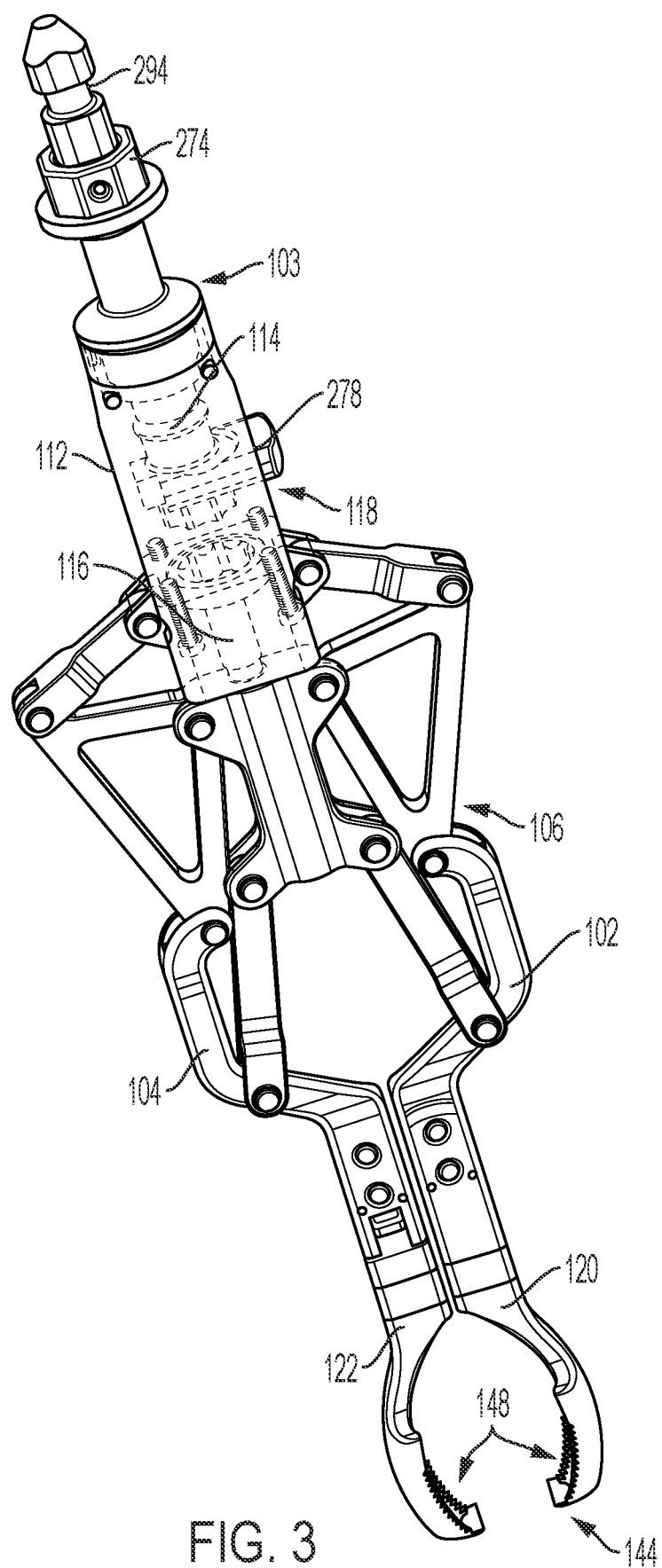
FIG. 3 is another perspective view of the surgical extractor of FIG. 1, with certain components omitted or rendered transparent for purposes of clarity.

With reference to FIG. 3, the surgical extractor 100 further includes a housing 112 housing a distal portion 114 of the tensioning shaft 110 and a proximal portion 116 of the driven shaft 108. In this exemplary embodiment, the housing includes a locking mechanism 118 for locking the position of the tensioning shaft 110 within the housing 112.

Figure 4A:
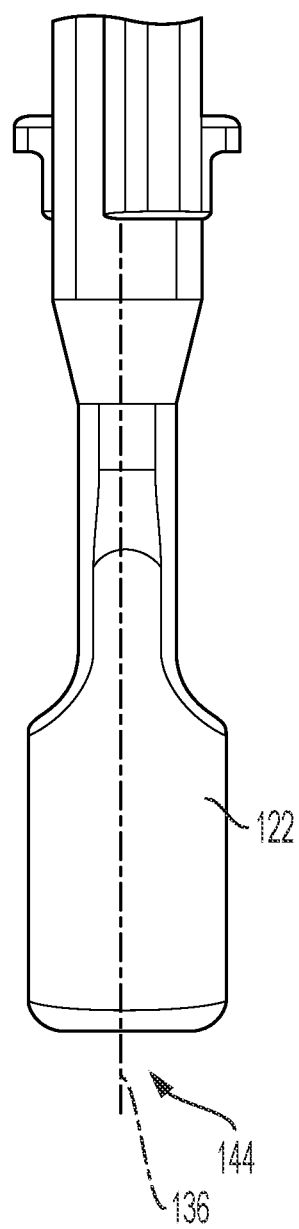
FIGS. 4A and 4B are exemplary jaws that can be used in accordance with the surgical extractor of FIG. 1.

Referring to FIGS. 1 and 3, the surgical extractor further includes a first jaw 120 attachable to a distal end of the first arm 102 and a second jaw 122 attachable to a distal end of the second arm 104. The first jaw 120 and the second jaw 122 according to this exemplary embodiment are configured as best shown in FIGS. 3 and 4A and provided with medial protrusions 128a, 128b, which define the distal end 144 of the jaw and allow the jaw to access and grip, e.g., a distal border of an implant 130 (e.g., a glenosphere). The jaws are curved e.g., concavely curved and/or spherically curved to provide clearance for an implant therein. A medial side or interior surface 148 is provided adjacent the medial protrusions 128a, 128b which, in this exemplary embodiment, include serrations 132a, 132b (FIG. 2) to facilitate gripping of the implant 130. Each of the first and second jaws include a proximal end having a joining face 138a, 138b for facing engagement with a respective first and second arm of the surgical extractor. Further, the first jaw's joining face 138a faces a direction opposite the second jaw's joining face 138b. For example, joining face 138a faces anteriorly while joining face 138b face posteriorly.

Figure 4B:
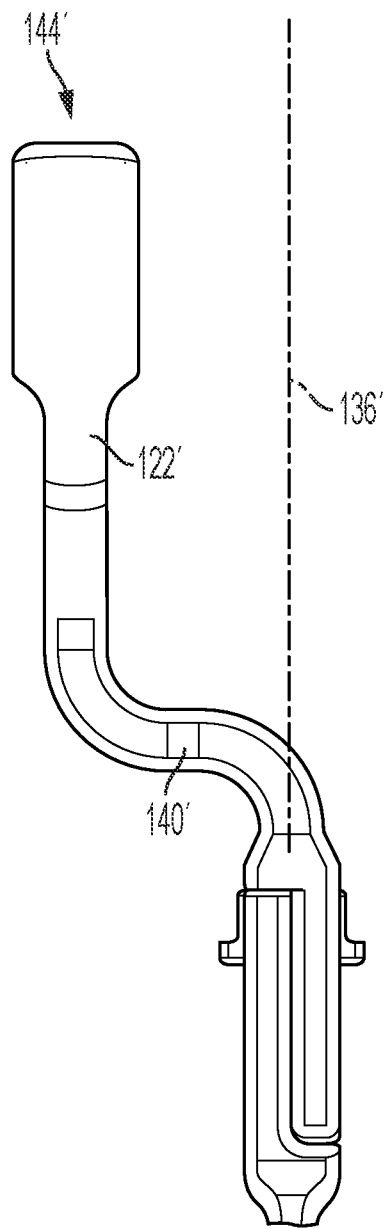

FIGS. 4A and 4B illustrate the first and second jaws of the surgical extractor of the subject disclosure. In this exemplary embodiment, the first and second jaws are configured as best shown in FIGS. 4A and 4B. The jaw 122 extends linearly towards its distal end 144 along a plane 136 defined by a joining face e.g., joining face 138a in FIG. 5, of the jaw 122.

FIG. 4B illustrates a jaw 122' in accordance with the subject disclosure. The jaw includes a segment 140' that laterally spaces the distal end 144' of the jaw a distance from a plane 136' defined by a joining face of the jaw at its proximal end.

The foregoing jaws are exemplary jaws applicable to the surgical extractor of the subject disclosure. However, other jaws and configurations suitable for other implants and sizes may be used. For example, the jaws may be oriented in other directions depending, for example, on the anatomical clearance available to access a particular implant. Alternative jaws can be readily selected and installed to the first and second arms at the time of use. Jaws may also be replaced as needed if broken during use.

Figure 5:
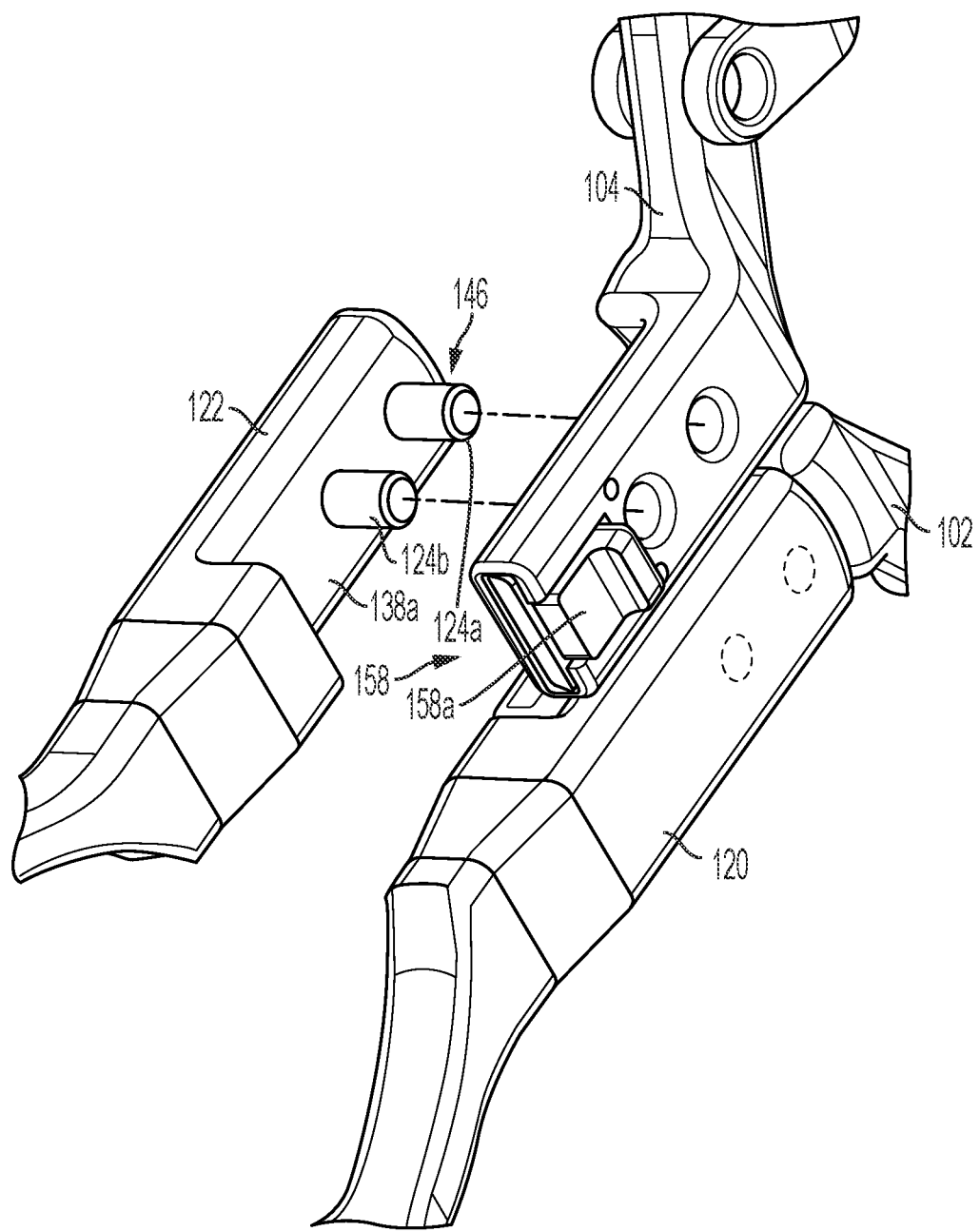
FIG. 5 is a perspective view of the engagement of the first and second arms to the first and second jaws of the surgical extractor of FIG. 1.
Figure 6:
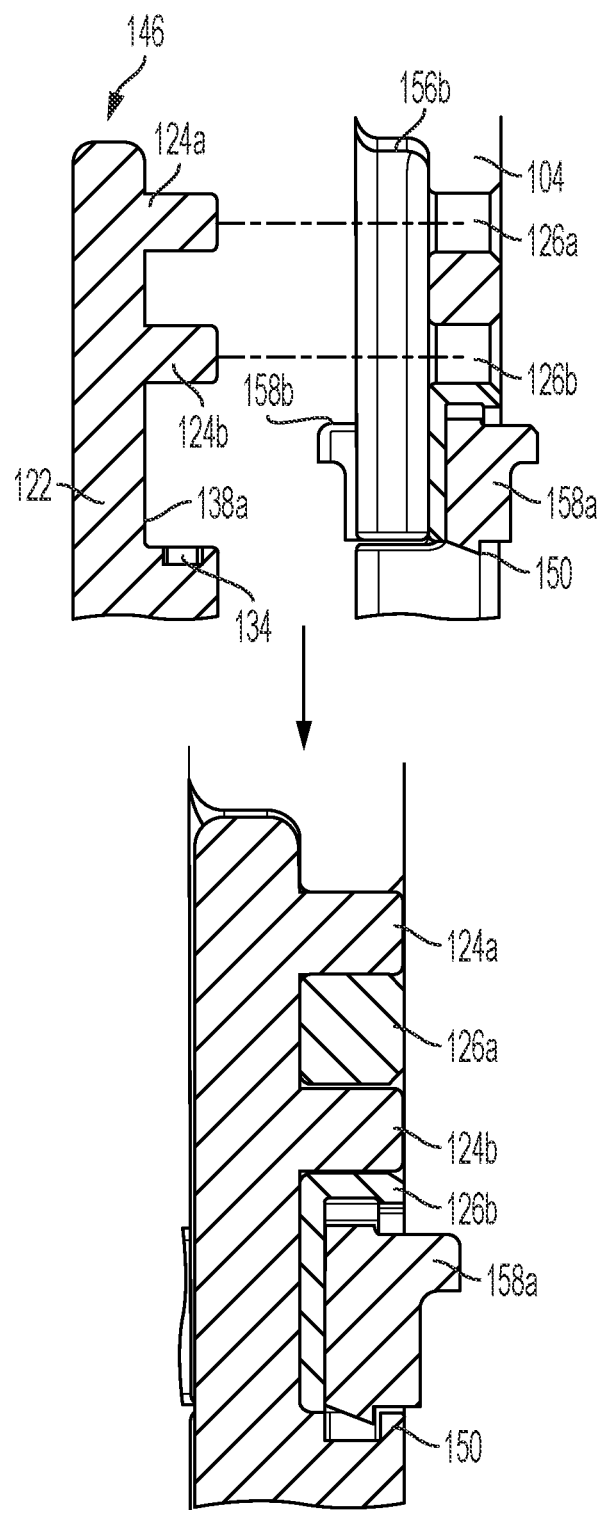
FIG. 6 is an elevation view of the engagement of the first and second arms to the first and second jaws of the surgical extractor of FIG. 1.
Figure 6A:
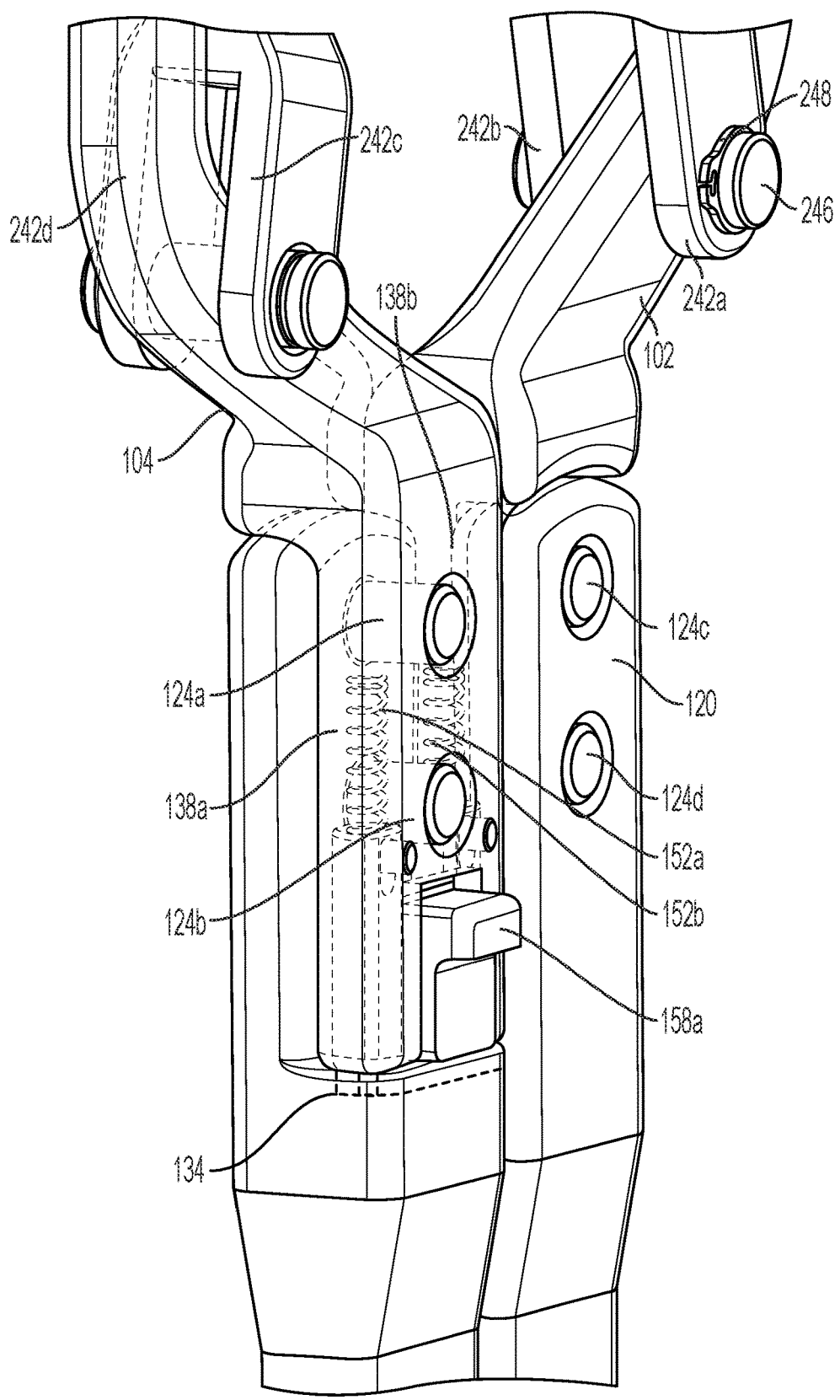
FIG. 6A is a perspective detailed view of the engagement of the first and second arms to the first and second jaws of the surgical extractor of FIG. 1, with certain components rendered transparent for purposes of clarity.

The exemplary embodiments of jaws disclosed herein are configured as push-to-connect jaws. In the present embodiments, each jaw includes jaw pins, such as jaw pins 124a, 124b of the second jaw 122, that protrude from the joining face 138a provided adjacent or about a proximal end 146 of the jaw 122, as best shown in FIG. 5. The jaw pins are sized to be accommodated by bores 126a, 126b located adjacent the distal end of the second arm 122, as best shown in FIGS. 6 and 6A. The first arm 102 is similarly provided with bores 126c, 126d to receive jaw pins 124c, 124d of the first jaw 120.

Figure 7:
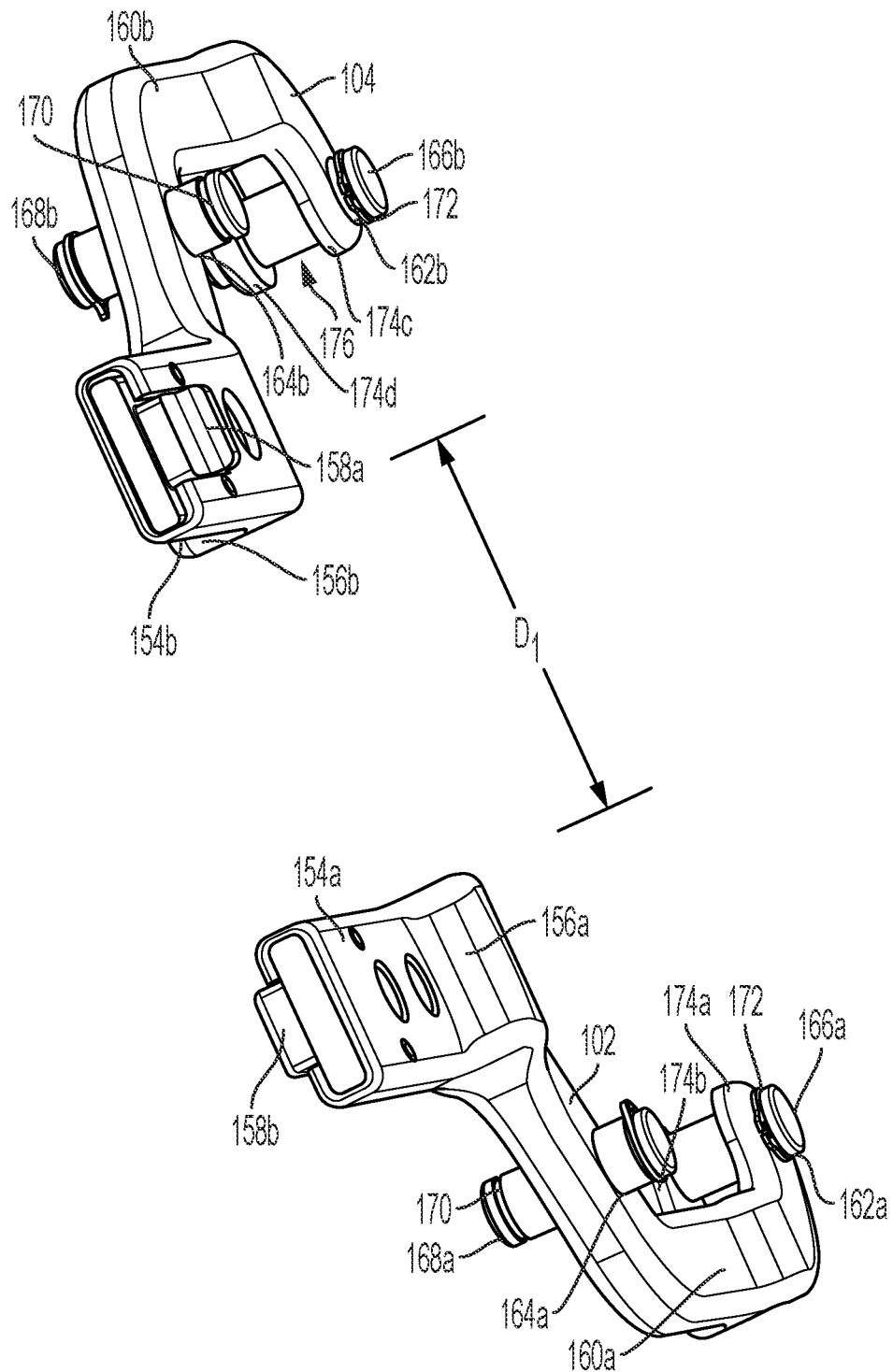
FIG. 7 is a bottom perspective view of a linkage assembly of the surgical extractor of FIG. 1 in a first position, with certain components omitted for purposes of clarity.
Figure 8:
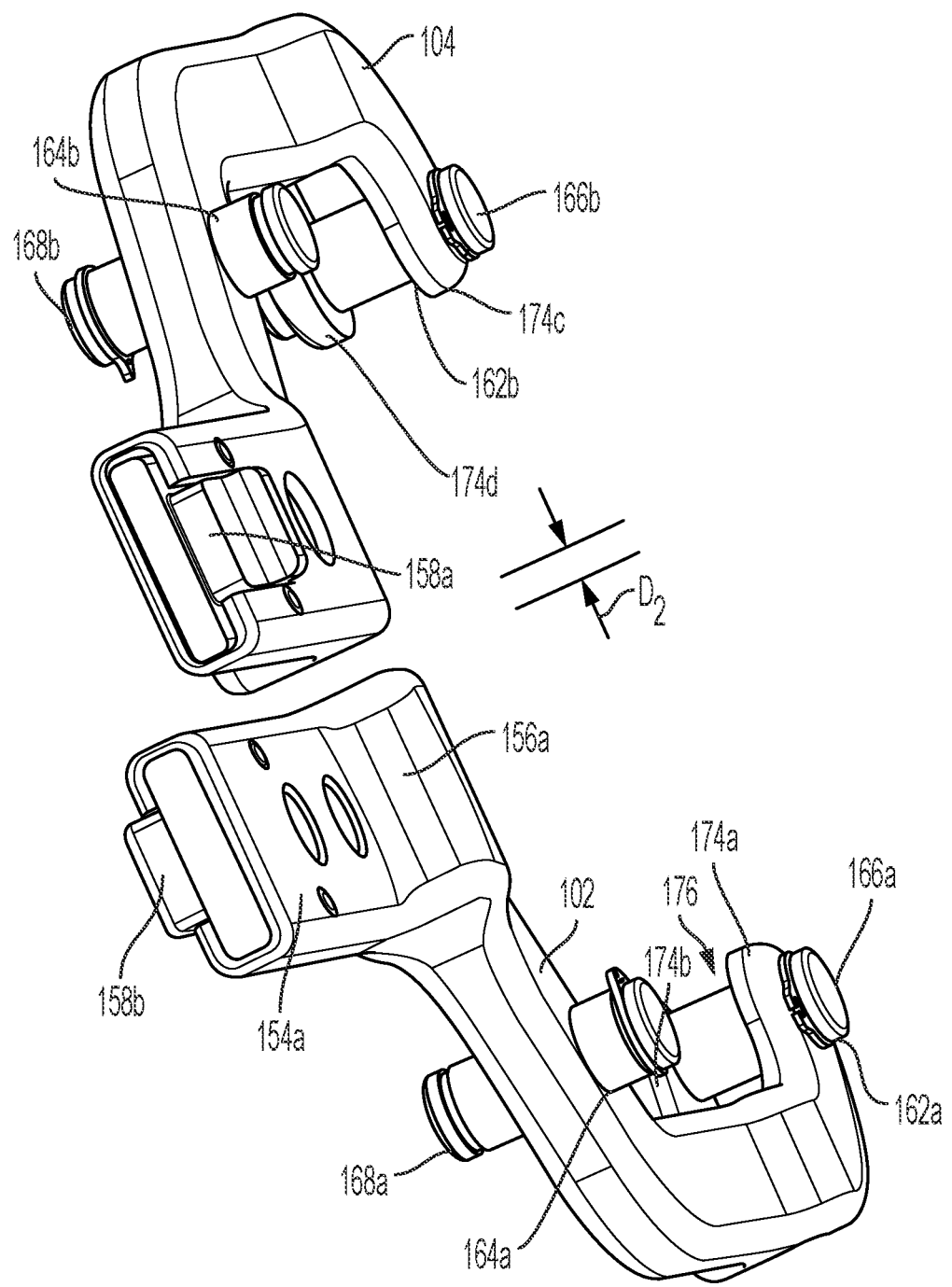
FIG. 8 is a bottom perspective view of the linkage assembly of the surgical extractor of FIG. 1 in a second position, with certain components omitted for purposes of clarity.

The first and second arms 102, 104 are configured as best shown in FIGS. 1, 7 and 8. The distal ends of the first arm 102 and the second arm 104 each include a linear segment having a planar face 154a, 154b sized to engage joining faces 138b, 138a of the first and second jaws, respectively. Each planar face is oriented to face an opposite direction, e.g., planar face 154a faces posteriorly and planar face 154b faces anteriorly. Respective stop surfaces or ledges 156a, 156b are provided adjacent a distal end of the planar faces and extend substantially perpendicular the planar faces 154a, 154b. The stop surfaces are sized and contoured to receive the proximal end 146 of the jaws. While the foregoing exemplary embodiment is configured with oppositely facing planar surfaces, other configurations can alternatively be provided, such as, for example, a configuration in which planar faces of the first and second arm face in the same direction, or in oppositely facing directions, such as medially and laterally.

Referring to FIGS. 5-6A, the distal ends of each of the first and second arms also include a locking mechanism 158 for releasably locking a jaws to the arm. The locking mechanism includes a lock button 158a housed within the arm. The lock button is biased by a biasing member, e.g., compression springs 152a, 152b, towards a locking position (FIG. 6). The lock button includes a projection 150 sized to fit within a recess 134 of the arm 104. As shown best in FIG. 6A, the bias of the compression springs 152a, 152b maintains the projection 150 within the recess 134 which, along with the jaw pins and bores, lock the jaw with the arm.

To attach the jaw, the jaw pins 124a, 124b are aligned with the corresponding bores 126a, 126b as shown in FIG. 5 and joined while moving the lock button 158a against the bias of the compression springs 152a, 152b. Once fully engaged, the lock button is released to allow the bias of the compression springs to move the projection 150 into engagement with the recess 134 to secure the jaw. The first arm 102 is attached to the first jaw 120 in the same fashion.

The first arm 102 and the second arm 104 respectively include curved proximal segments. In the present exemplary embodiment, the curved proximal segments are substantially "C"-shaped arms 160a, 160b and e.g., oriented in mirror-like fashion, and include bores 162a, 162b at its proximal end and bores 164a, 164b at its distal end sized to receive proximal arm linkage shafts 166a, 166b and distal arm linkage shafts 168a, 168b, as shown in FIGS. 7-8. The proximal and distal arm linkage shafts can be provided with grooves 170 sized to accommodate retention rings 172, which can be provided as necessary to retain other links of the linkage assembly 106.

The proximal ends of the first and second arms each include a pair of fingers 174a, 174b and 174c, 174d, e.g., spaced apart fingers that provide a clearance or channel 176 therebetween for receiving another linkage member operatively connected to respective proximal linkage shafts, with the respective fingers being located on the outside of the received linkage member.

The first and second arms intersect the distal arm linkage shafts 168a, 168b at a middle portion along its longitudinal length, the distal arm linkage shafts, and first and second arms sized at this location to allow room to accommodate a second pair of fingers of like or similar size (i.e., fingers 242c, 242d in FIG. 6A) in a sandwich-like arrangement.

Figure 9:
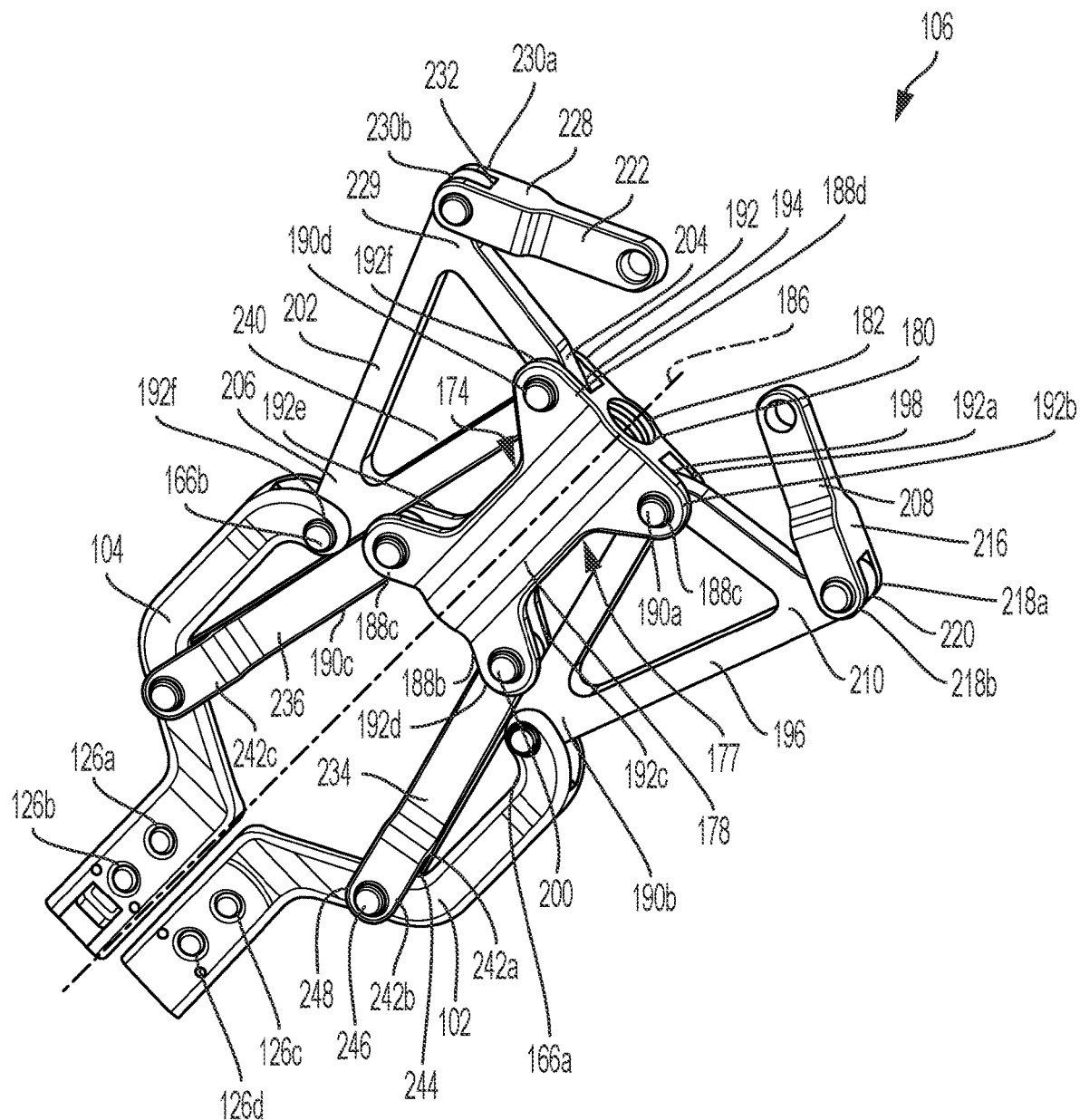
FIG. 9 is a perspective view of the linkage assembly of the surgical extractor of FIG. 1.
Figure 10:
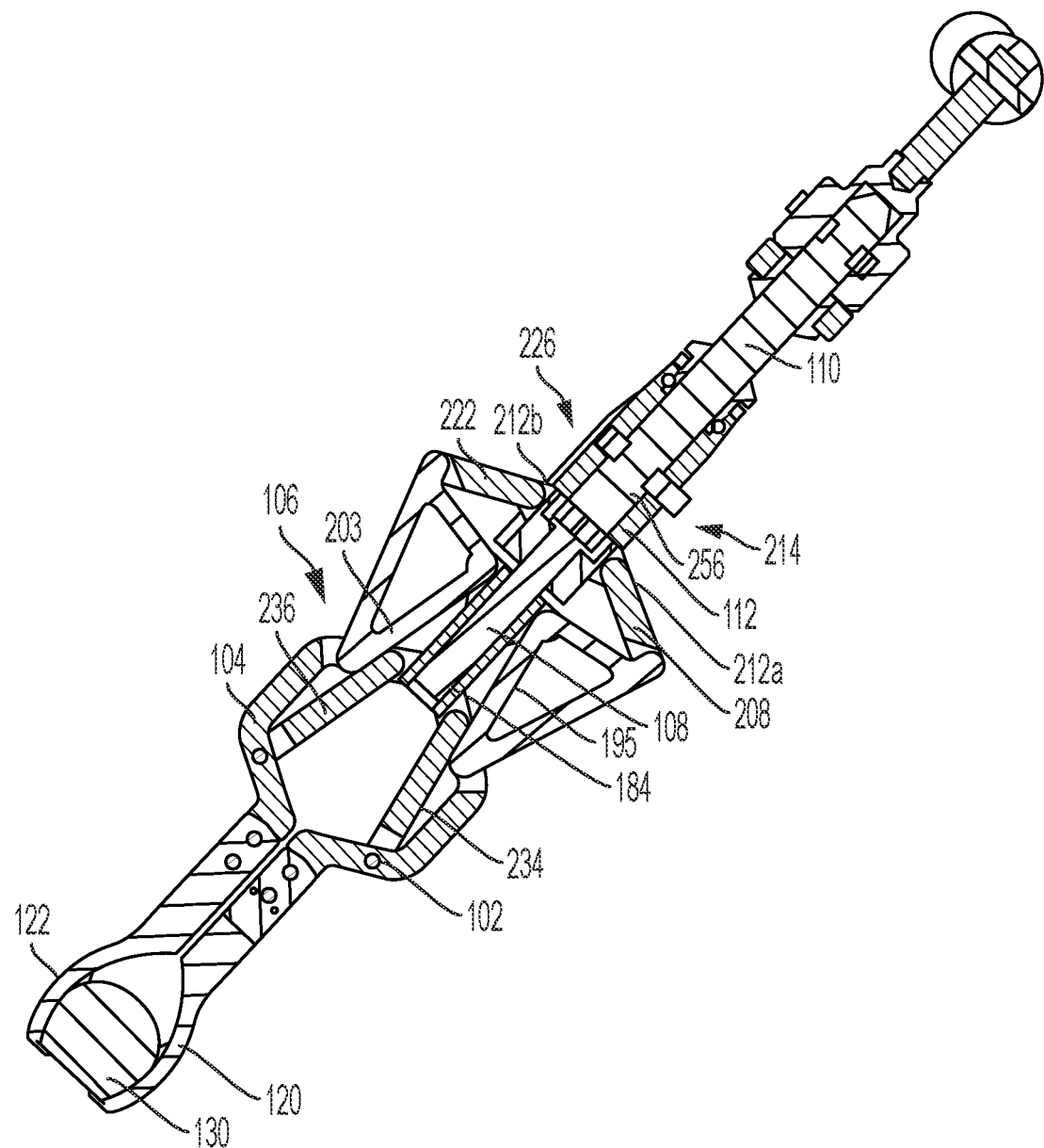
FIG. 10 is a longitudinal cross-sectional view of the surgical extractor of FIG. 1.

The linkage assembly 106 is best shown in FIGS. 1, 9, and 10. In this exemplary embodiment, the linkage assembly 106 includes a plurality of links. More particularly, the linkage assembly includes a central link 178 that includes a bore 180 sized to receive the driven shaft 108 and running the entire longitudinal length of the central link along a centerline 186 of the central link and the linkage assembly itself. The central link 178 includes a first side 177 and a second side 179 opposite the first side. The bore 180 includes internal threads 182 complementary to external threads 184 provided on the driven shaft 108 (see also FIG. 11). The central link 108 includes four flanges 188a-d along the periphery of the central link that each include holes sized to receive central link linkage shafts 190a-d. Each of the flanges 188a-d includes a pair of fingers 192a-b, 192c-d, 192e-f, 192g-h, each with a channel 194 provided therebetween sized to accommodate another linkage member. In the present exemplary embodiment, owing to the flanges 188a-d, the central link has a longitudinal anterior-posterior cross-section having a substantially butterfly-like shape.

The linkage assembly 106 further includes a first triangular link 196 having a first corner 198 pivotably connected to the first side of the central link at its proximal end via the central link linkage shaft 190a and a second corner 200 pivotably connected to a proximal end of the first arm 102 via the proximal arm linkage shaft 166a. Arranged likewise with respect to the central link in a mirror-like fashion from centerline 186, a second triangular link 202 is attached to the second side of the central link. As shown in FIG. 9, the second triangular link 202 includes a first corner 204 pivotably connected to the second side of the central link about its proximal end via the central link linkage shaft 190d and a second corner 206 pivotably connected to a proximal end of the second arm 104, via the proximal arm linkage shaft 166b. In this exemplary embodiment, the first triangular link 196 and the second triangular link 202 have a uniform, rectangular longitudinal cross-sectional shape, though other configurations can be provided.

The linkage assembly 106 further includes a first drive link 208 having a distal end pivotably connected to a third corner 210 of the first triangular link 196 and a proximal end pivotably connected to the housing 112 via a flange 212a located about a first side 214 of the housing 112. The proximal end of the first drive link is of a substantially uniform, rectangular longitudinal cross-sectional shape, expanding to a greater width along a portion 216 towards its distal end, where it forms two fingers 218a, 218b and a channel 220 at its distal end, similar to the fingers 192 and channels 194 discussed above in connection with the first arm 102 and the second arm 104.

Arranged likewise with respect to the central link 178 in a mirror-like fashion from centerline 186, a second drive link 222 is attached to the housing. Similar to the first drive link, the second drive link 222 includes a distal end pivotably connected to a third corner 224 of the second triangular link 202 and a proximal end pivotably connected to the housing 112 via a flange 212b located about a second side 226 of the housing 112. As with the first drive link, the proximal end of the second drive link 222 is of a uniform, rectangular cross-sectional shape, expanding to a greater width along a portion 228 towards its distal end, where it forms two fingers 230a, 230b and a channel 232 at the distal end of the second drive link.

The linkage assembly 106 further includes a first strut link 234 and a second strut link 236. The first strut link includes a proximal end pivotably connected to the first side 177 of the central link 178 via flange 188b and linkage shaft 190b and a distal end pivotably connected to the first arm 102 via linkage shaft 168a. The second strut link 236 includes a proximal end pivotably connected to the second side 179 of the central link 178 via flange 188c and linkage shaft 190c, and a distal end pivotably connected to the second arm 104 via linkage shaft 168b.

An engagement is formed between a proximal portion of the first strut link 234 and a distal portion of an inner side 195 of the first triangular link 196 such that the first strut link 234 is in sliding or pivoting engagement with the first triangular link 196. Likewise, an engagement is formed between a proximal portion of the second strut link 236 and a distal portion of an inner side 203 (FIG. 10) of the second triangular link 202 such that the second strut link 236 is in sliding or pivoting engagement with the second triangular link 202. The first strut link 234 and the second strut link 236 are each of a uniform rectangular longitudinal cross-sectional shape along the engagements 238 and 240 and extend toward their distal ends where it expands to include two fingers 242a-d on each strut link and a channel 244 therebetween sized to accommodate the first and second arms 102, 104, respectively.

In like manner as described above in connection with the proximal and distal arm linkage shafts 166a-b, 168a-b, grooves 170 and retention rings 172 of the linkage assembly 106 are joined throughout by linkage shafts and retention rings, such as linkage shaft 246 and retention ring 248, as shown, for example, in FIG. 6A and FIG. 9, to engage the first strut link 234 with the first arm 102.

Figure 11:
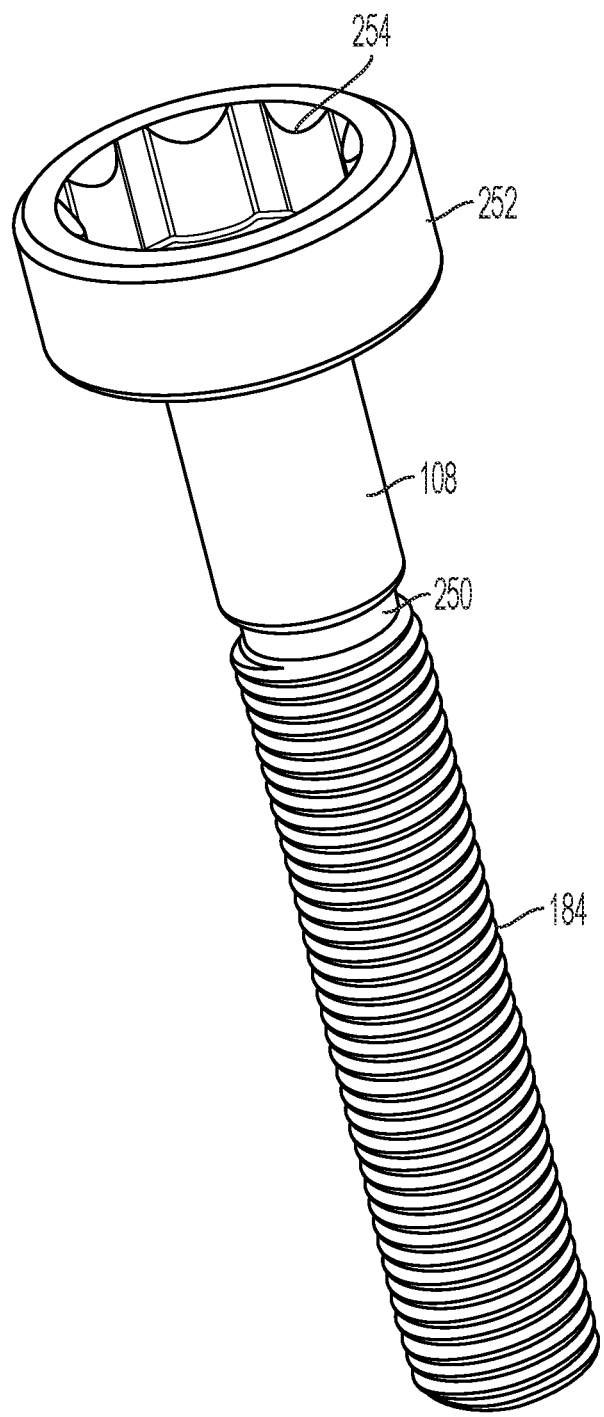
FIG. 11 is a perspective view of a driven shaft of the surgical extractor of FIG. 1.
Figure 12:
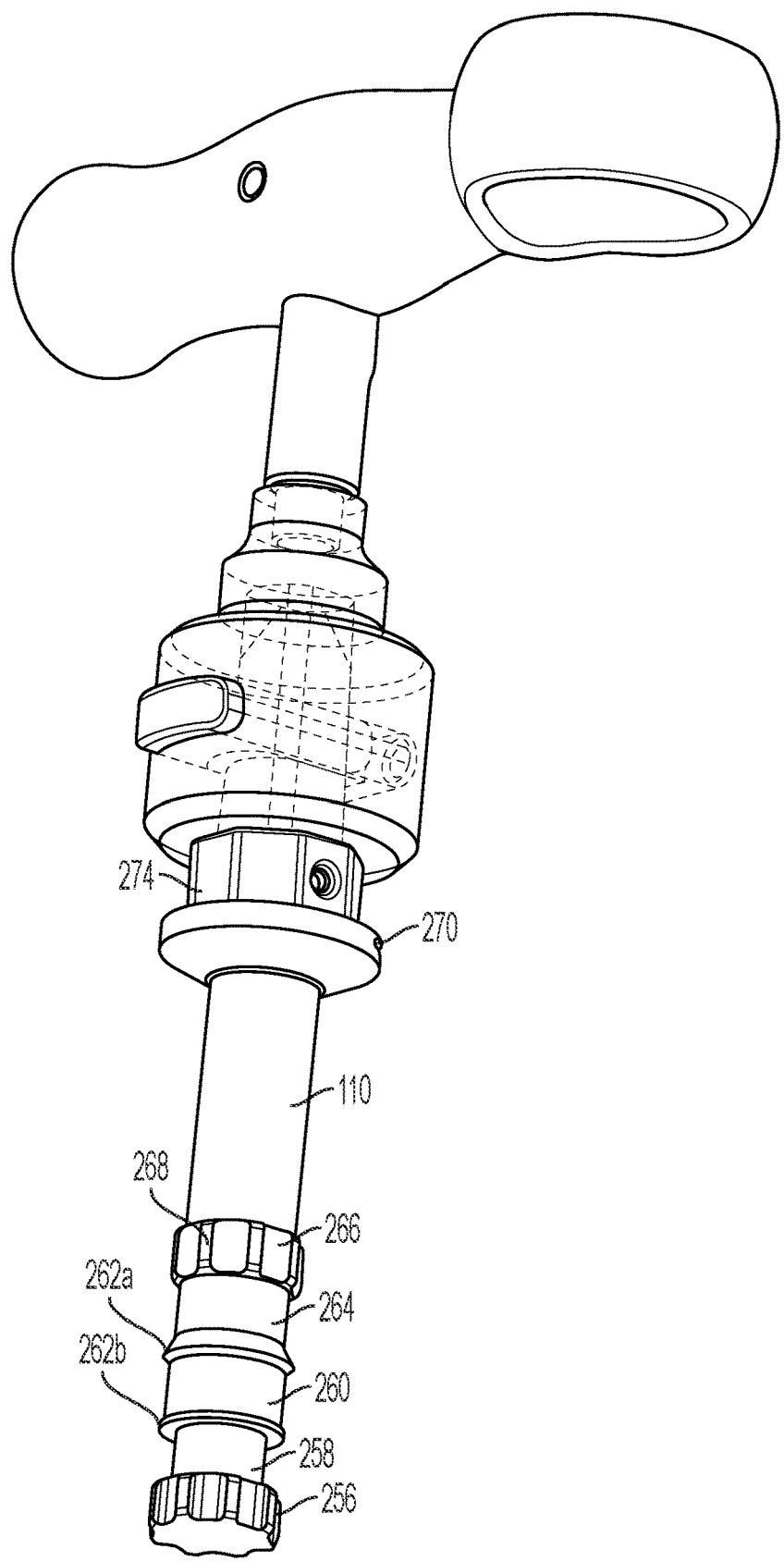
FIGS. 12, 12A and 12B are perspective views of the orthopedic implant extraction tool of FIG. 1, shown with certain components isolated, omitted or rendered transparent for purposes of clarity.

The driven shaft 108 is shown best in FIGS. 10 and 11, and includes threads 184 shaped complimentary to the threads 182 located about the bore 180 of the central link 178. The driven shaft is shaped to be received by the bore 180 of the central link to house the driven shaft along the threaded portion. A recess 250 is provided along the proximal boundary of the threads 184. The proximal end of the driven shaft includes a head 252 having a socket 254. As shown in FIG. 12, the socket 254 is complementary to a driver head 256 located about the distal end of the tensioning shaft 110.

The driven shaft 108 is operatively engaged with the linkage assembly 106 (e.g., threadedly engaged) for moving the linkage assembly between first and second positions. For example, the driven shaft 108 is moved relative to the linkage assembly from a first position such that the first and second arms 102, 104 are separated by a first distance D1 as shown in FIG. 7, to a second position in which the first and second arms 102, 104 are separated by a second distance D2, as shown in FIG. 8. This movement between the first position and the second position in turn provides a clamping force that can be applied, for example, by the first and second jaws 120, 122 to an implant 130.

The first and second arms 102, 104, and the first and second jaws 120, 122 move between first and second positions in a relatively linear (in-line) path, as opposed to an arcing path. Stated differently, jaws remain substantially parallel or parallel to each other as they are moved between first and second positions. This provides operational advantages, as it will not matter if the jaws are clamping on a large implant or a small implant, the geometry of the jaws will be aligned at the best angle. In contrast, for most devices in which the clamping jaws are based on a pivot, then the angle of the jaws with respect to the implant will be different depending on whether the jaws are clamping to a large implant or a small implant.

For example, as once an operator places the first and second jaws 120, 122 in the first position (FIG. 7), they are assured that the surgical extractor 100 can be easily placed in the second position (FIG. 8), as the straightest and most direct path between two points is a straight line. Conversely, a more-severe arcing path would increase the likelihood of anatomical obstacles, or the implant itself, obscuring clearance between the jaws and the desired gripping portion of the implant, thereby hindering the attempted extraction.

Figure 13A:
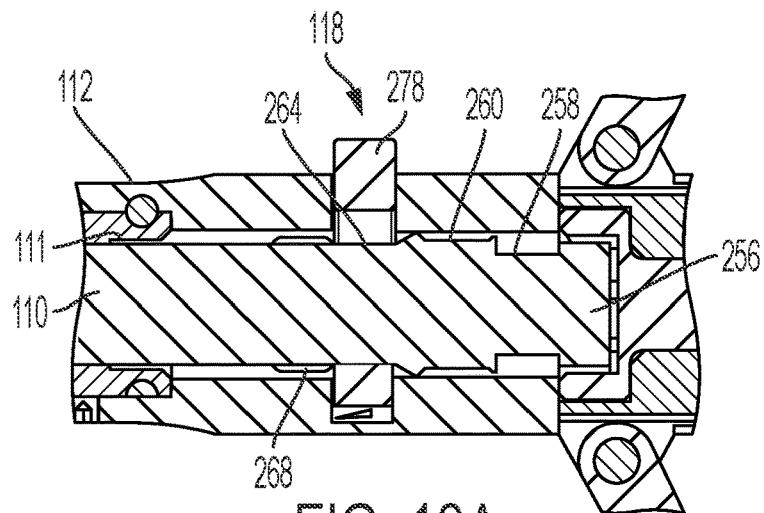
FIGS. 13A, 13B and 13C are partial side views of the orthopedic implant extraction tool of FIG. 1 in various positions, with certain components omitted for purposes of clarity.

With reference to FIGS. 12-13A-C, the tensioning shaft 110 includes an annular groove 258 about its distal end sized to engage and lockingly receive a locking mechanism 118, discussed in greater detail below, for locking the position of the tensioning shaft within the housing 112. The tensioning shaft also includes an intermediate section 260 of relatively larger diameter than a main body portion of the tensioning shaft and bounded by annular ridges 262a, 262b. Another intermediate section 264 is provided adjacent the annular ridge 262a that is bounded proximally by a splined section 266 of similar shape as the driver head 256 and which has splines 268 complementary in shape to the driver head splines. About its distal end, the tensioning shaft includes a driver head 256 that includes splines complementary in shape to the socket 254 so as to cooperatively engage the socket 254 e.g., matingly engages with the socket.

Figure 12A:
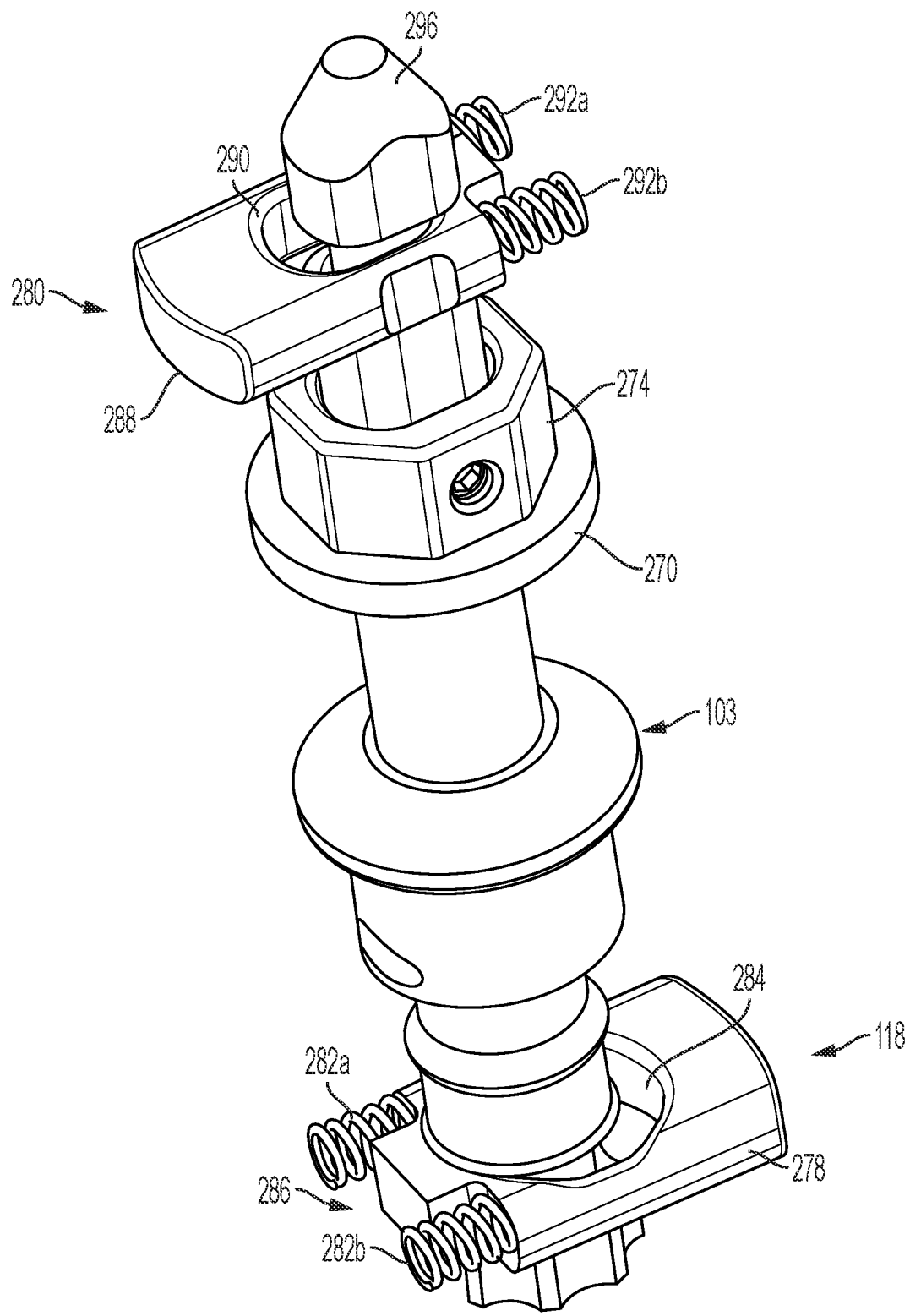
Figure 12B:
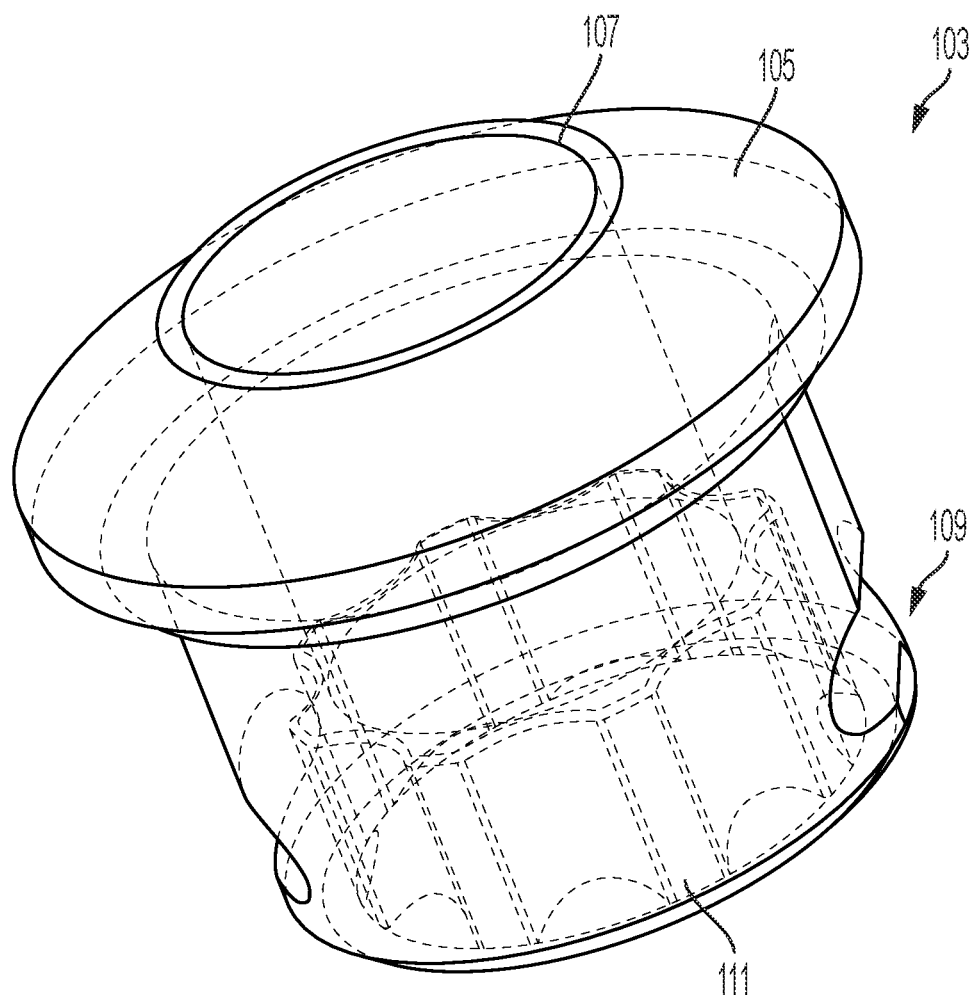

Certain components of the housing in FIG. 12A have been omitted to better illustrate a cap 103 that defines the proximal end of the housing, also shown in greater detail in FIG. 12B. The cap 103 includes a face, e.g., a proximally facing face 105, and a bore 107 along a centerline of the cap and running the longitudinal length of the cap. The bore 107 is sized to receive the tensioning shaft 110 and, along a distal section 109 of the cap, the bore is provided with grooves or splines 111 sized complimentary to the splines 268 of the splined section 266 of the tensioning shaft 110. When the tensioning shaft 110 is fully retracted within the housing, corresponding to the positions shown in FIG. 13C, the splines 268 of the splined section 266 engage with the grooves 111 of cap 103.

The locking mechanism 118 and a T-shaft locking mechanism 280 are shown in detail in FIGS. 12A and 13A-C. The locking mechanism 118 includes a slide 278 biased by a biasing member e.g., compression springs 282a, 282b. The slide includes an orifice 284 that is sized larger than the diameter of sections 258, 260 and 264 of the tensioning shaft. The bias of the compression springs 282a, 282b normally biases an end 286 of the slide against sections 258, 260 or 264 of the tensioning shaft 110. The annular recess 258 is sized to arrest axial and rotational movement when received by end 286 of the slide under the normal bias of the compression springs 282a, 282b. The slide 278 extends outside the perimeter of the housing 112, as shown best in FIG. 3 and is capable of manual manipulation against the bias of the compression springs.

Figure 13B:
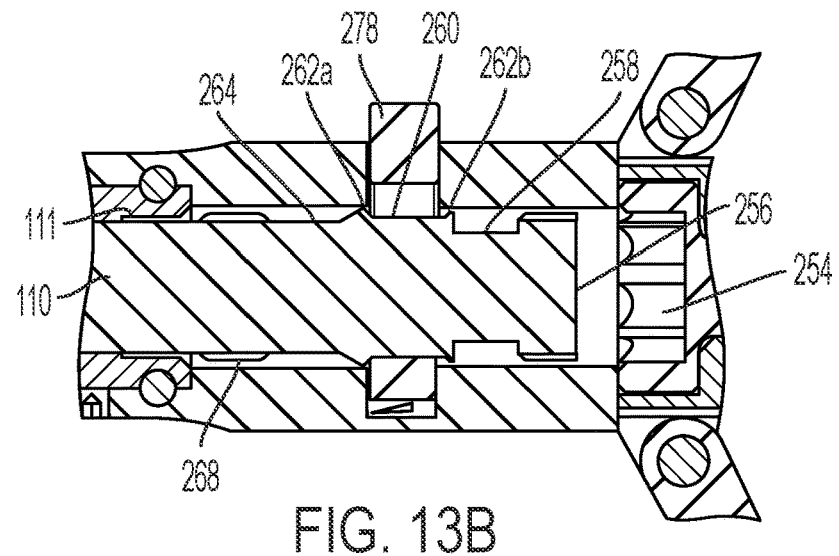
Figure 13C:
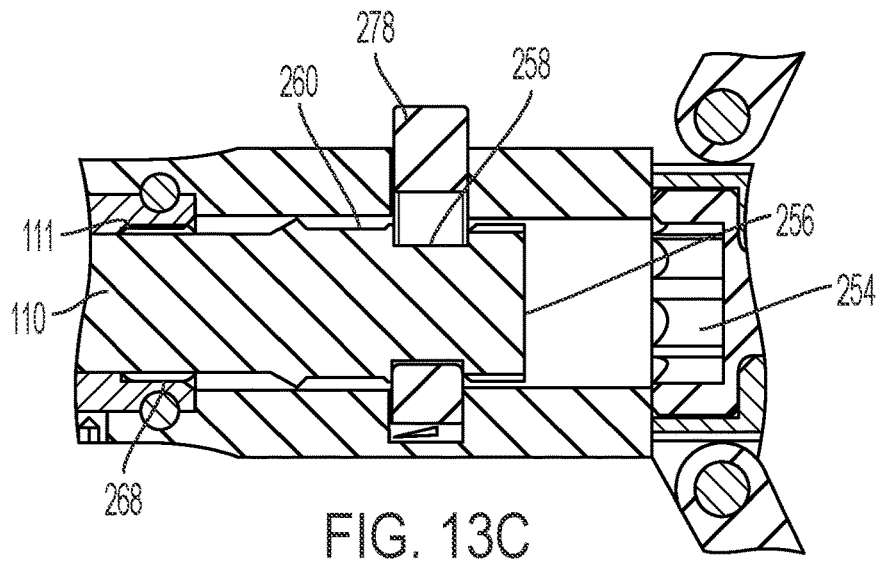

As shown in FIGS. 13A-C, the tensioning shaft 110 is movable within the housing 112 between multiple positions, e.g., between three distinct positions. In a first or tensioning position shown in FIG. 13A, the driver head 256 of the tensioning shaft 110 engages the socket of the driven shaft 108 to provide rotational tension to the driven shaft to move the shaft further distally or proximally relative to the central link.

In a second or an adjustment position shown in FIG. 13B, the slide 278 of the locking mechanism 118 is positioned within section 260 of the tensioning shaft, where the tensioning shaft can rotate freely without engaging the driven shaft 108, allowing an operator to select a rotational position of the extractor's proximal end (e.g., handle) that is comfortable before beginning the extraction. Axial movement in this adjustment position is hindered (but not impossible) due to annular ridges 262a, 262b, that directs force towards a rotational force to allow easy rotating of the T-handle 298. Stated differently, the annular ridges 262a, 262b act a detent to provide a (limited) amount of resistance to disengagement from the adjustment mode and allowing the user tactile feedback such that he or she knows the device is in this adjustment mode.

In a third or lock position shown in FIG. 13C, the slide 278 of the locking mechanism 118 engages the tensioning shaft 110 to releasably secure the tensioning shaft within the housing 264 to lock the tensioning shaft against axial movement. When the tensioning shaft is retracted into this position, the splines 268 of the splined section 266 engages with the grooves 111 located in the bore 107 of the cap 103 to the housing 112 to lock the tensioning shaft 110 against rotational movement (see also FIGS. 12-12B). This lock position is released only upon pressing the slide 278 against the bias of the compression springs 282a, 282b.

Figure 14:
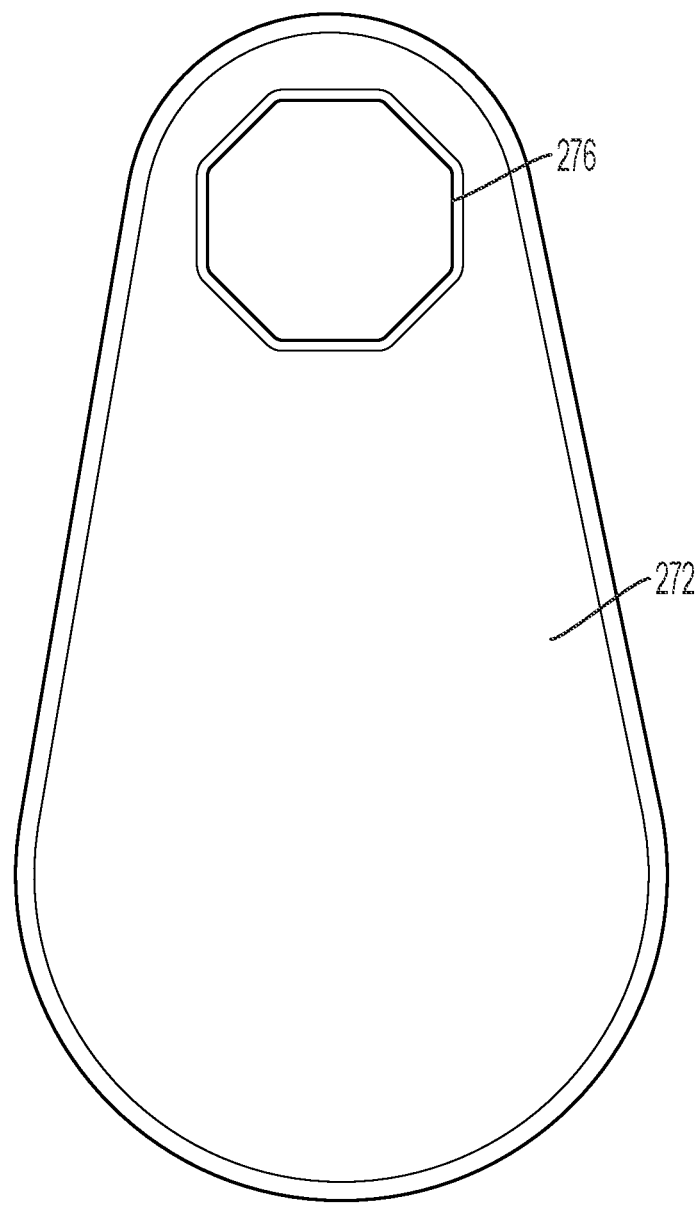
FIG. 14 is a plan view of a strike plate of the surgical extractor of FIG. 1.
Figure 16:
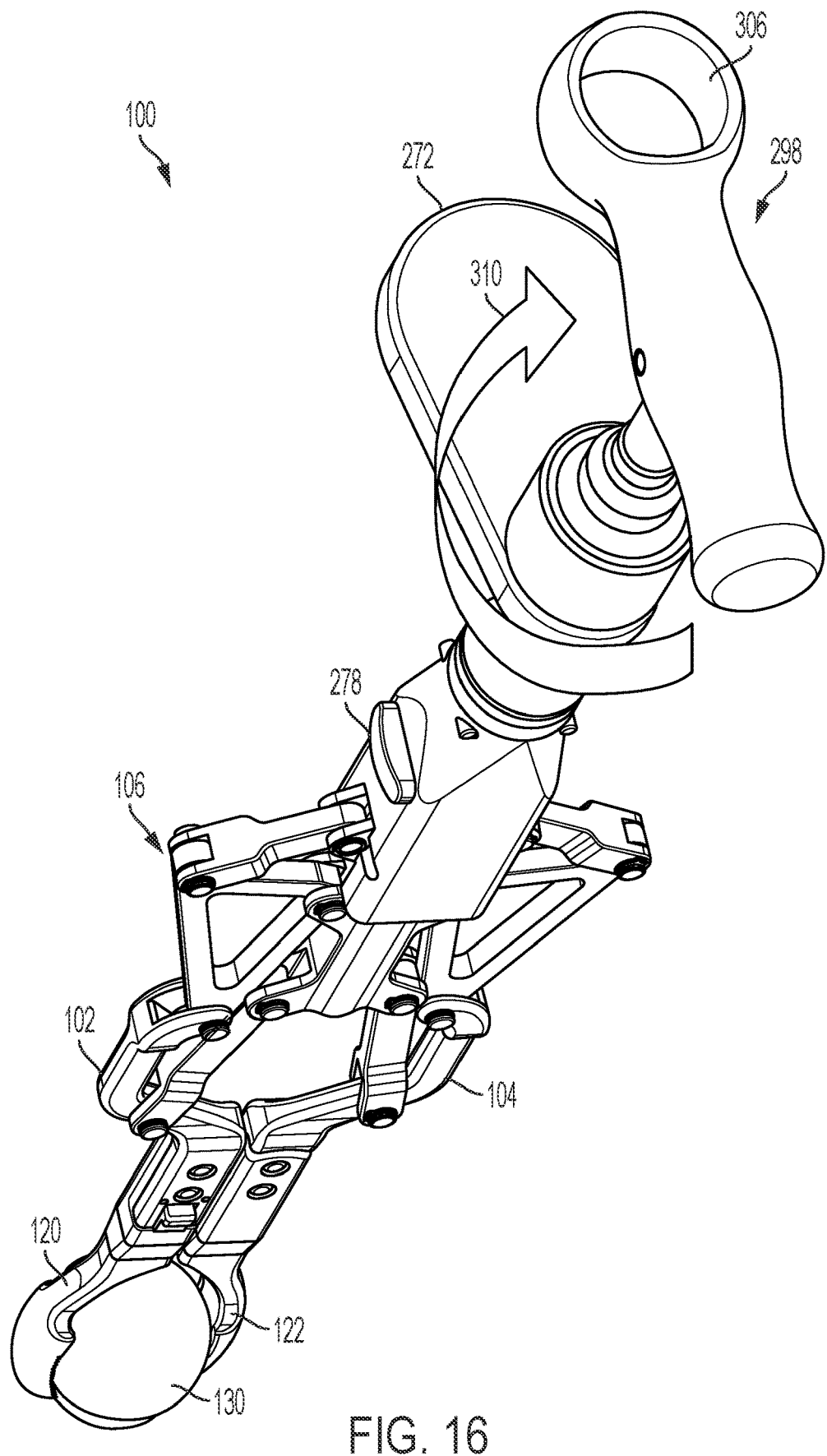
FIG. 16 is a perspective view of the surgical extractor of FIG. 1 in operation.

The tensioning shaft 110 further includes a flange base 270 about its proximal end that serves as a base for a strike plate 272, as shown in FIGS. 14 and 16. A strike plate head 274 is provided on the tensioning shaft 110 above the flange base 270 shaped complimentary to an orifice 276 on the strike plate 272. Specifically, the strike plate head is shaped to have a polygonal shape or be multisided, and the orifice is configured to be complementary in shape to that of the strike plate head such that it is polygonal in shape or is multisided. In this exemplary embodiment, the orifice 276 has 8-sides to provide 8 different rotational positions or angles for the strike plate 272. The proximal end of the tensioning shaft is defined by a truncated conical tip 296 having a racetrack cross-sectional shaped main body portion.

Figure 15:
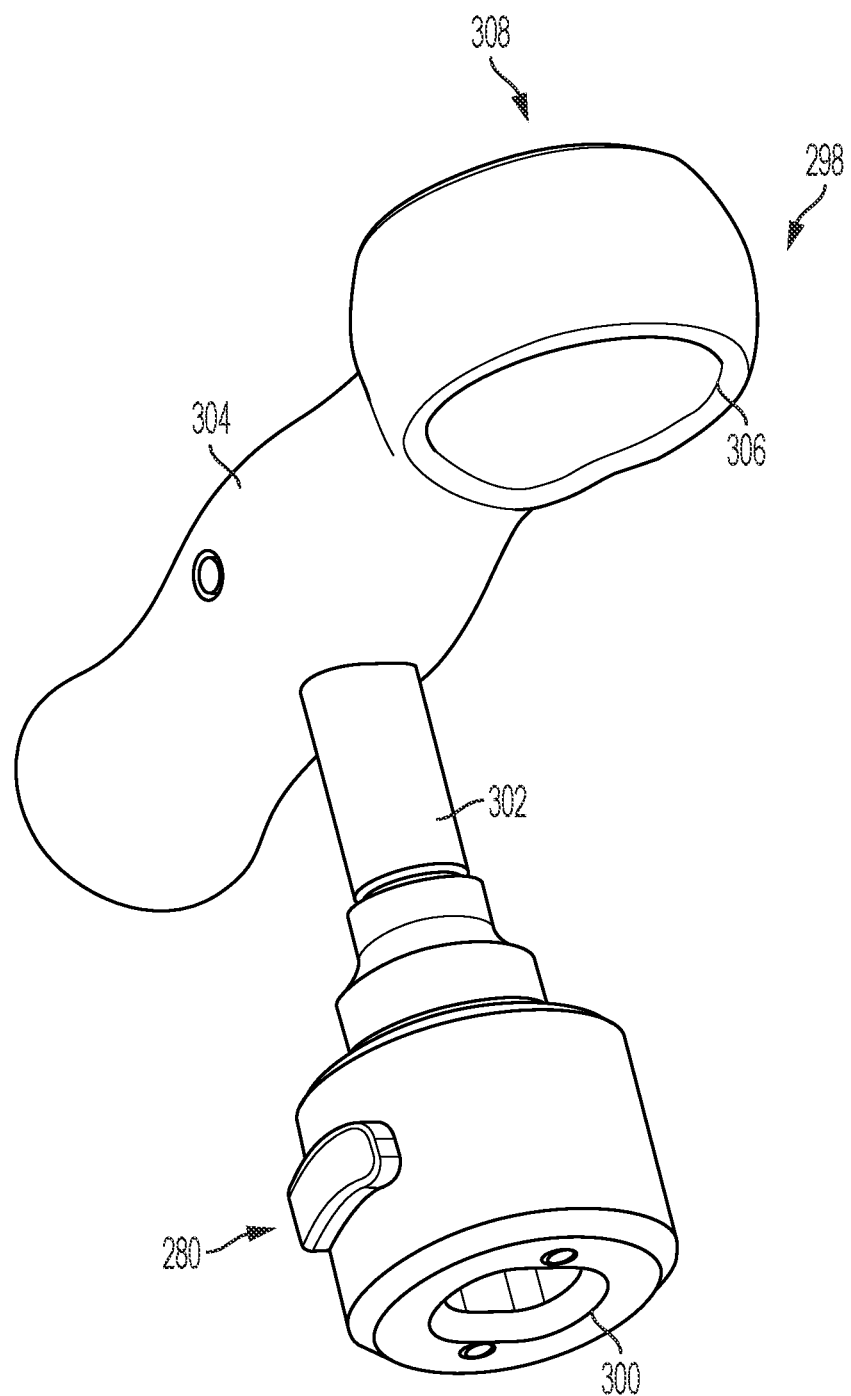
FIG. 15 is a perspective view of a T-handle of the surgical extractor of FIG. 1.

The surgical extractor further includes a handle about its proximal end. The handle in the present exemplary embodiment is a T-handle 298, as best shown in FIG. 15. The T-handle includes a handle 304 and a shaft 302 extending from the handle. The distal end of the shaft includes a quick connect having an orifice 300 with a racetrack shape sized to receive the conical tip 296 of the tensioning shaft. The quick connect further includes a T-lock locking mechanism 280, as further discussed below. The handle 304 is configured as best shown in FIG. 15 and includes a through hole 306 about a lateral end 308, sized to receive a finger or shaft to easily turn the T-handle.

Referring back to FIG. 12A, a T-lock locking mechanism 280 is, in this exemplary embodiment, of similar construction to the locking mechanism 118, and similarly includes a slide 288, an orifice 290, and compression springs 292a, 292b. The slide 288 is received within annular recess 294 of the tensioning shaft 110 to lock the T-handle 298 onto the tensioning shaft and allow rotation thereof. Upon pressing slide 288, the T-handle 298 can be removed from the tensioning shaft. Securing the T-handle into place, along with flange base 270, secures the strike plate 272 about the strike plate head 274, to lock the strike plate in place.

Operation of the surgical extractor 100 will now be described in connection with FIG. 16. The T-handle 298 is secured about the proximal end of the tensioning shaft. The linkage assembly is in an initial position, such as shown in FIG. 7, in which the first and second arms 102, 104 are separated by a distance greater than the diameter of the implant to be removed and the tensioning shaft is in the lock position, such as shown in FIG. 13C. Slide 278 is pressed and the tensioning shaft is advanced to the first position as shown in FIG. 13A. The T-handle 298 is then rotated in a clockwise direction 310 which drives rotation of the driven shaft which in turn moves the linkage assembly 106 into a second position as shown in FIG. 16. In the second position the first and second arms are closer together so that jaws 120, 122 grip the outer periphery of the implant 130. The linkage assembly of the present surgical extractor provides a mechanical advantage for providing a clamping force owing to the overall cantilever forces provided by the various linkages of the surgical extractor. Further, due to the mechanical linkage design of the present surgical extractor the distal ends of the jaws advantageously move in a substantially lateral direction as opposed to a substantially arced direction as in conventional extractor designs, and move in a manner wherein the jaws are substantially parallel to each other at all times, which allows for easier use and positioning of the surgical extractor, especially during clamping of the implant.

Once the jaws 120 and 122 tightly grip the implant 130 the operator pulls the T-handle to disengage the driver head 256 from the driven shaft 108, and places the tension shaft 110 into the second position shown in FIG. 13B and rotates the T-handle and strike plate to a comfortable position for performing the extraction. The tension shaft is then placed into the third or lock position shown in FIG. 13C and the strike plate 272 is positioned about the strike plate head 274 of the tensioning shaft 110 at a desired rotational position and the strike plate is struck with a surgical hammer (not shown) to remove the implant 130.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

The invention claimed is:
1. A surgical extractor comprising:
a first arm and a second arm;
a linkage assembly comprising a plurality of links, wherein the linkage assembly is connected to each of the first and second arms at two locations along a length of each of the first and the second arms via separate unique links of the plurality of links;
a driven shaft operatively engaged with the linkage assembly for moving the linkage assembly between a first position such that the first arm and the second arm are separated by a first distance and a second position such that the first arm and the second arm are separated by a second, smaller distance to provide a clamping force; and
a tensioning shaft engageable with the driven shaft for moving the driven shaft relative to the linkage assembly, wherein the tensioning shaft is movable between (a) a locked position wherein the tensioning shaft is disengaged from the driven shaft and locked against axial movement and (b) a tensioning position wherein the tensioning shaft engages the driven shaft to allow for tension to be applied to the driven shaft.

2. The surgical extractor of claim 1, wherein the tensioning shaft is movable between an adjustment position wherein the tension shaft is axially movable relative to the linkage assembly between the locked position and the tensioning position.

3. The surgical extractor of claim 1, further comprising a housing containing the tensioning shaft and the driven shaft.

4. The surgical extractor of claim 3, wherein the tensioning shaft is movable within the housing between the locked position and the tensioning position.

5. The surgical extractor of claim 3, wherein the tensioning shaft extends through a proximal end of the housing and the driven shaft extends through a distal end of the housing.

6. The surgical extractor of claim 3, wherein the housing further comprises a lock for releasably securing the tensioning shaft within the housing in the locked position.

7. The surgical extractor of claim 6, wherein the tensioning shaft includes an annular groove that engages the lock for locking a position of the tensioning shaft within the housing in the locked position.

8. The surgical extractor of claim 1, wherein the linkage assembly comprises a central link housing the driven shaft.

9. The surgical extractor of claim 8, wherein the central link is threadedly engaged with the driven shaft.

10. The surgical extractor of claim 1, wherein the plurality of links includes:
a central link;
a first triangular link having a first corner pivotably connected to a first side of the central link, and a second corner pivotably connected to the first arm;
a second triangular link having a first corner pivotably connected to a second side of the central link, and a second corner pivotably connected to the second arm;
a first drive link having a distal end pivotably connected to a third corner of the first triangular link and a proximal end; and
a second drive link having a distal end pivotably connected to a third corner of the second triangular link and a proximal end.

11. The surgical extractor of claim 10, wherein the plurality of links further includes:
a first strut link having a proximal end pivotably connected to the first side of the central link and a distal end pivotably connected to the first arm; and
a second strut link having a proximal end pivotably connected to the second side of the central link and a distal end pivotably connected to the second arm.

12. The surgical extractor of claim 1, wherein a proximal end of the driven shaft includes a socket.

13. The surgical extractor of claim 1, wherein a distal end of the tensioning shaft includes a driver head for operatively engaging the driven shaft.

14. The surgical extractor of claim 1, further comprising:
a first jaw attachable to a distal end of the first arm; and
a second jaw attachable to a distal end of the second arm.

15. The surgical extractor of claim 14, further comprising an assembly for releasably connecting the first jaw to the first arm, the assembly comprising a spring-biased projection.

16. The surgical extractor of claim 15, wherein the assembly further comprises a recess shaped to receive the spring-biased projection.

17. The surgical extractor of claim 1, further comprising a handle assembly attachable to the tensioning shaft.

18. The surgical extractor of claim 17, wherein the handle assembly includes a T-handle having a handle and a through hole located in proximity to a lateral end of the handle.

19. The surgical extractor of claim 1, further comprising a strike plate extending from a proximal end of the tensioning shaft.

20. A surgical extractor for extracting orthopedic implants comprising:
a housing;
a first arm and a second arm;
a linkage assembly connected to the first and second arms;
a driven shaft housed within the housing and operatively engaged with the linkage assembly for moving the linkage assembly; and
a tensioning shaft housed within the housing and engageable with the driven shaft for moving the driven shaft relative to the linkage assembly,
wherein the linkage assembly includes:
a central link,
a first triangular link having a first corner pivotably connected to a first side of the central link, and a second corner pivotably connected to the first arm,
a second triangular link having a first corner pivotably connected to a second side of the central link, and a second corner pivotably connected to the second arm,
a first drive link having a distal end pivotably connected to a third corner of the first triangular link and a proximal end pivotably connected to the housing, and
a second drive link having a distal end pivotably connected to a third corner of the second triangular link and a proximal end pivotably connected to the housing.

21. The surgical extractor of claim 20, wherein the driven shaft threadedly engages the central link to move between first and second positions, wherein in the first position the first and second arms are spaced apart a first distance and in the second position, the first and second arms are spaced apart a second distance less than the first distance.

* * * * *